United States Patent
Eyal

(10) Patent No.: US 11,524,042 B2
(45) Date of Patent: Dec. 13, 2022

(54) METHODS FOR THE PRODUCTION OF DIFFERENT CANNABIS PRODUCT COMPOSITIONS

(71) Applicant: BUZZELET DEVELOPMENT AND TECHNOLOGIES LTD., Or-Akiva (IL)

(72) Inventor: Aharon M. Eyal, Jerusalem (IL)

(73) Assignee: BUZZELET DEVELOPMENT AND TECHNOLOGIES LTD., Or-Akiva (IL)

( * ) Notice: Subject to any disclaimer, the term of this patent is extended or adjusted under 35 U.S.C. 154(b) by 108 days.

(21) Appl. No.: 15/762,899

(22) PCT Filed: Sep. 26, 2016

(86) PCT No.: PCT/IB2016/055755
§ 371 (c)(1),
(2) Date: Mar. 23, 2018

(87) PCT Pub. No.: WO2017/051398
PCT Pub. Date: Mar. 30, 2017

(65) Prior Publication Data
US 2018/0280459 A1    Oct. 4, 2018

Related U.S. Application Data

(60) Provisional application No. 62/233,355, filed on Sep. 27, 2015.

(51) Int. Cl.
*A61K 36/185* (2006.01)
*A61K 31/352* (2006.01)
*A61K 31/05* (2006.01)

(52) U.S. Cl.
CPC ............ *A61K 36/185* (2013.01); *A61K 31/05* (2013.01); *A61K 31/352* (2013.01); *A61K 2236/00* (2013.01); *A61K 2236/10* (2013.01); *A61K 2236/33* (2013.01); *A61K 2236/39* (2013.01)

(58) Field of Classification Search
CPC ....................................................... A61K 36/00
USPC ........................................................... 424/725
See application file for complete search history.

(56) References Cited

U.S. PATENT DOCUMENTS

| 2010/0119606 A1 | 5/2010 | Whittle et al. |
| 2014/0271940 A1 | 9/2014 | Wurzer |

FOREIGN PATENT DOCUMENTS

WO    2015/068052    5/2015

OTHER PUBLICATIONS

International Search Report in International Patent Application No. PCT/IB2016/055755, dated Jan. 19, 2017.

*Primary Examiner* — Michael V Meller
(74) *Attorney, Agent, or Firm* — Alphapatent Associates, Ltd; Daniel J. Swirsky

(57) ABSTRACT

Methods for the production of different *cannabis* product compositions. Method for the production of at least two different *cannabis* product compositions from a solid *cannabis* plant material are described including providing a solid *cannabis* plant material containing at least one cannabinoid and at least one terpene at cannabinoid to terpene weight/weight ratio R100; first extracting from said solid *cannabis* plant material a first composition comprising at least 10% but less than 90% of said cannabinoid and at least 1% of said terpene at cannabinoid to terpene weight/weight ratio R101, wherein R101 differs from R100 by at least 10%; second extracting from said solid *cannabis* plant material a second composition comprising at least 10% of said cannabinoid and at least 1% of said terpene at cannabinoid to terpene weight/weight ratio R102, wherein R102 differs from R101 by at least 10%; and optionally refining said first composition, said second composition, or both.

1 Claim, No Drawings

METHODS FOR THE PRODUCTION OF DIFFERENT CANNABIS PRODUCT COMPOSITIONS

CROSS-REFERENCE TO RELATED APPLICATIONS

The present application claims the benefit of U.S. Provisional Application Ser. No. 62/233,355 filed Sep. 27, 2015, the disclosure of which is expressly incorporated by reference herein in its entirety.

BACKGROUND

Many indications are being treated with medical *cannabis* and more indications will be added in the coming future. Medical *cannabis* is used in various forms, such smoking, vaporization, extracted oil, etc. Each one of those forms provides dozens of compounds to the user. It is claimed that multiple of those components are active and that there is synergism between some of the active forms. Different indications require different *cannabis* compositions. Additionally, it is suggested that similar compositions have different effects on different patients.

There is therefore great need for generating a large variety of *cannabis* compositions to help find the most desired effect for every indication and every patient. The industry typically addresses this need by genetically developing more and more strains in order to increase the selection. Such development of strains is expensive, complicated and takes time to form the required product.

The methods of the present invention achieve that goals through an alternative method that costs much less, is easy to conduct and adds new compositions within hours or less.

SUMMARY OF THE INVENTION

A method for the production of at least two different *cannabis* product compositions from a solid *cannabis* plant material is described including providing a solid *cannabis* plant material containing at least one cannabinoid and at least one terpene at cannabinoid to terpene weight/weight ratio R100; first extracting from said solid *cannabis* plant material a first composition comprising at least 10% but less than 90% of said cannabinoid and at least 1% of said terpene at cannabinoid to terpene weight/weight ratio R101, where R101 differs from R100 by at least 10%; second extracting from said solid *cannabis* plant material a second composition comprising at least 10% of said cannabinoid and at least 1% of said terpene at cannabinoid to terpene weight/weight ratio R102, where R102 differs from R101 by at least 10%; and optionally refining said first composition, said second composition, or both.

Addition embodiments include: the method described above where said solid *cannabis* plant material contains a first cannabinoid and a second cannabinoid at first cannabinoid to second cannabinoid weight/weight ratio of R110; said first composition comprises said first cannabinoid and said second cannabinoid at first cannabinoid to second cannabinoid weight/weight ratio of R111, where R111 differs from R110 by at least 10%; and said second composition comprises said first cannabinoid and said second cannabinoid at first cannabinoid to second cannabinoid weight/weight ratio of R112, where R112 differs from R111 by at least 10%; the method described above where said first cannabinoid is tetrahydrocannabinol and said second cannabinoid is cannabidiol; the method described above where R112 differs from R110 by at least 10%; the method described above where said cannabinoid is tetrahydrocannabinol or cannabidiol or combinations thereof; the method described above where said terpene is selected from the group consisting of pinenes, limonene, linalool, caryophyllene, myrcene, humulene, borneol, eucalyptol, terpineol and mixtures thereof; the method described above including drying said solid *cannabis* plant material prior to extracting; the method described above where including heating said solid *cannabis* plant material prior to or simultaneously with extracting in order to effect decarboxylation of the cannabinoid; the method described above where said solid *cannabis* plant material contains at least two cannabinoids, and further comprising heating the plant material to selectively decarboxylate one of the cannabinoids prior to or simultaneously with said first extracting; the method described above where said solid *cannabis* plant material contains at least two cannabinoids, and further comprising heating the plant material to selectively decarboxylate one of the cannabinoids prior to or simultaneously with said second extracting; the method described above where said first extracting, said second extracting or both comprise at least one of distillation and contacting with an extractant; the method described above where the distillation is steam distillation; the method described above where the method described above where said first extracting, said second extracting or both comprise continuous, counter-current contacting with an extractant; the method described above where said first extracting comprises contacting with a first extractant selected from the group consisting of water, alkanols, super-critical $CO_2$, sub-critical $CO_2$, alkanes, alkenes, liquefied alkanes, liquefied alkenes, liquefied ethers, and mixtures thereof; the method described above where said second extracting comprises contacting with a second extractant selected from the group consisting of water, alkanols, super-critical $CO_2$, sub-critical $CO_2$, alkanes, alkenes, liquefied alkanes, liquefied alkenes, liquefied ethers, and mixtures thereof; the method described above where said first extracting comprises contacting with a first extractant, said second extracting comprises contacting with a second extractant and said first extractant is substantially the same as the second extractant; the method described above where said first extracting comprises contacting with a first extractant comprising two solvents at a given weight/weight ratio, and said second extracting comprises contacting with a second extractant comprising the same two solvents at a different weight/weight ratio; the method described above including heating said first composition, said second composition or both at a temperature and for time sufficient to effect at least partial decarboxylation; the method described above where R102 differs from R100 by at least 10%; the method described above where R100 is in the range between 1:10 and 500:1; the method described above including fractionating said first composition into a third composition with cannabinoid to terpene weight/weight ratio R103 and a fourth composition with cannabinoid to terpene weight/weight ratio R104, where R103 differs from R104 by at least 10%; the method described above including fractionating said second composition into a fifth composition with cannabinoid to terpene weight/weight ratio R105 and a sixth composition with cannabinoid to terpene weight/weight ratio R106, where R105 differs from R106 by at least 10%; the method described above where said first composition comprises a first cannabinoid and a second cannabinoid, the first cannabinoid to second cannabinoid weight/weight ratio in said third composition is R113, the first cannabinoid to second cannabinoid weight/weight ratio in said fourth composition is R114, and 8113 differs from R114 by at least 10%; and the method described above where said second composition comprises a first cannabinoid and a second cannabinoid, the first cannabinoid to second cannabinoid weight/weight ratio in said fifth composition is R115, the first cannabinoid to second cannabinoid weight/weight ratio in said sixth composition is R116, and R115 differs from R116 by at least 10%.

A method for the production of at least two different *cannabis* product compositions from a *cannabis* plant material is also described including providing a solid *cannabis* plant material containing at least one cannabinoid and at least one terpene; first extracting said plant material to form a first extract comprising at least 10% of said cannabinoid and at least 1% of said terpene at cannabinoid to terpene weight/weight ratio R200; fractionating said first extract to form a first composition comprising at least 10% of the cannabinoid of said first extract and at least 1% of the terpene of said first extract at cannabinoid to terpene weight/weight ratio R201, where R201 differs from R200 by at least 10%; and a second composition comprising at least 10% of said first extracted cannabinoid and at least 1% of said first extracted terpene at cannabinoid to terpene weight/weight ratio R202; where R202 differs from R201 by at least 10%; and optionally refining said first composition, said second composition or both.

Additional embodiments include: the method described above where said plant material contains a first cannabinoid and a second cannabinoid; said first extract comprises said first cannabinoid and said second cannabinoid at first cannabinoid to second cannabinoid weight/weight ratio of R210; said first composition comprises said first cannabinoid and said second cannabinoid at first cannabinoid to second cannabinoid weight/weight ratio of R211 where R211 differs from R210 by at least 10%; and said second composition comprises said first cannabinoid and said second cannabinoid at first cannabinoid to second cannabinoid weight/weight ratio of R212, where R212 differs from R211 by at least 10%; the method described above additionally including second extracting said plant material to form a second extract comprising at least 10% of said cannabinoid and at least 1% of said terpene; the method described above where said cannabinoid is tetrahydrocannabinol or cannabidiol or combinations thereof; the method described above where said terpene is selected from the group consisting of pinenes, limonene, linalool, caryophyllene, myrcene, humulene, borneol, eucalyptol, terpineol and combinations thereof; the method described above additionally including drying said solid *cannabis* plant material prior to said first extracting; the method described above additionally including heating said solid *cannabis* plant material prior to or simultaneously with said first extracting; the method described above where said solid *cannabis* plant material contains at least two cannabinoids, and further comprising heating the plant material to selectively decarboxylate one of the cannabinoids prior to or simultaneously with said first extracting; the method described above where said first extract comprises at least two cannabinoids, further comprising heating the first extract to selectively decarboxylate one of the cannabinoids prior to or simultaneously with said fractionating; the method described above where said first extracting, said second extracting or both comprise at least one of distillation and contacting with an extractant; the method described above where the distillation is steam distillation; the method described above where said first extracting, said fractionating or both comprise continuous, counter-current contacting with an extractant; the method described above where said first extracting comprises contacting with an extractant selected from the group consisting of water, alkanols, super-critical $CO_2$, sub-critical $CO_2$, alkanes, alkenes, liquefied alkanes, liquefied alkenes, liquefied ethers, and mixtures thereof; the method described above where said fractionating comprises contacting with an extractant selected from the group consisting of water, alkanols, super-critical $CO_2$, sub-critical $CO_2$, alkanes, alkenes, liquefied alkanes, liquefied alkenes, liquefied ethers, and mixtures thereof; the method described above where said first extracting comprises contacting with a first extractant, said fractionating comprises contacting with a second extractant and said first extractant is substantially the same as said second extractant; the method described above where said first extracting comprises contacting with a first extractant comprising two solvents at a given weight/weight ratio, and said fractionating comprises contacting with a second extractant comprising the same two solvents at a different weight/weight ratio; the method described above where said fractionating comprises at least one of contacting with a second extractant, ion-exchanging, chromatographic separation and/or distilling; the method described above additionally including heating said first composition, said second composition, or both at a temperature and for time sufficient to effect at least partial decarboxylation; the method described above where R202 differs from R200 by at least 10%; the method described above where R200 is in the range between 1:10 and 500:1; the method described above where said first cannabinoid is tetrahydrocannabinol and said second cannabinoid is cannabidiol; and the method described above where R212 differs from R210 by at least 10%.

A method for the production of at least two different *cannabis* product compositions from a solid *cannabis* plant material is also described including providing a solid *cannabis* plant material containing at least one cannabinoid and at least one terpene at cannabinoid to terpene weight/weight ratio R300; first extracting said solid *cannabis* plant material to form: a first composition comprising at least 10% but less than 90% of said cannabinoid and at least 1% of said terpene at cannabinoid to terpene weight/weight ratio R301, where R301 differs from R300 by at least 10%; and a residual solid *cannabis* second composition; separating said first composition from the residual solid *cannabis* plant second composition, which residual composition comprises at least 10% of said cannabinoid and at least 1% of said terpene at cannabinoid to terpene weight/weight ratio R302, where R302 differs from R301 by at least 10%.

Additional embodiments include: the method described above where R302 differs from R300 by at least 10%; the method described above where said provided solid *cannabis* plant material contains a first cannabinoid and a second cannabinoid at first cannabinoid to second cannabinoid weight/weight ratio of R310; said first composition comprises said first cannabinoid and said second cannabinoid at first cannabinoid to second cannabinoid weight/weight ratio of R311, where R311 differs from R310 by at least 10%; and said residual composition comprises said first cannabinoid and said second cannabinoid at first cannabinoid to second cannabinoid weight/weight ratio of R312, where R312 differs from R311 by at least 10%; the method described above where said first cannabinoid is tetrahydrocannabinol and said second cannabinoid is cannabidiol; the method described above where R312 differs from R310 by at least 10%; the method described above where said cannabinoid is tetrahydrocannabinol or cannabidiol or combinations thereof; the method described above where said terpene is selected from the group consisting of pinenes, limonene, linalool, caryophyllene, myrcene, humulene, borneol, eucalyptol, terpineol and mixtures thereof; the method described above further comprising drying said solid *cannabis* plant material prior to extracting; the method described above additionally including heating said solid *cannabis* plant material prior to or simultaneously with extracting; the method described above where said *cannabis* plant material comprises at least two cannabinoids, and further comprising heating the provided solid plant material to selectively decarboxylate one of the cannabinoids prior to or simultaneously with said first extracting; the method described above where said first extracting, said second extracting or both comprise at least one of distillation and contacting with an extractant; the method described above where the distillation is steam distillation; the method described above where said first extracting, said fractionating or both comprise continuous, counter-current contacting with an extractant the method described above where said first extracting comprises contacting with a first extractant selected from the group consisting of water, alkanols, super-critical $CO_2$, sub-critical $CO_2$, alkanes, alkenes, liquefied alkanes, liquefied alkenes, liquefied ethers, and mixtures thereof; the method described above additionally including heating of said first composition at a temperature and for time sufficient to effect at least partial decarboxylation; the method described above where R300 is in the range between 1:10 and 500:1; the method described above additionally including fractionating said first composition into a third composition with cannabinoid to terpene weight/weight ratio R303 and a fourth composition with cannabinoid to terpene weight/weight ratio R304, where R303 differs from R304 by at least 10%; and the method described above where said first composition comprises a first cannabinoid and a second cannabinoid, first cannabinoid to second cannabinoid weight/weight ratio in said third composition is R313, first cannabinoid to second cannabinoid weight/weight ratio in said fourth composition is R314, and R313 differs from R314 by at least 10%.

At least two different *cannabis* product compositions from a solid *cannabis* plant material produced by a method including providing a solid *cannabis* plant material containing at least one cannabinoid and at least one terpene at cannabinoid to terpene weight/weight ratio R100; first extracting from said solid *cannabis* plant material a first composition comprising at least 10% but less than 90% of said cannabinoid and at least 1% of said terpene at cannabinoid to terpene weight/weight ratio R101, where R101 differs from R100 by at least 10%; second extracting from said solid *cannabis* plant material a second composition comprising at least 10% of said cannabinoid and at least 1% of said terpene at cannabinoid to terpene weight/weight ratio R102, where R102 differs from R101 by at least 10%; and optionally refining said first, said second composition, or both.

At least two different *cannabis* product compositions from a solid *cannabis* plant material are also described produced by a method including providing a solid *cannabis* plant material containing at least one cannabinoid and at least one terpene at cannabinoid to terpene weight/weight ratio R300; first extracting said solid *cannabis* plant material to form a first composition comprising at least 10% but less than 90% of said cannabinoid and at least 1% of said terpene at cannabinoid to terpene weight/weight ratio R301, where R301 differs from R300 by at least 10%, and a residual solid *cannabis* second composition; separating said first composition from the residual solid *cannabis* plant second composition, which residual composition comprises at least 10% of said provided solid plant material cannabinoid and at least 1% of said provided solid plant material terpene at cannabinoid to terpene weight/weight ratio R302, where R302 differs from R301 by at least 10%.

The above compositions are also described deposited on a solid carrier.

Definitions

The term cannabinoid refers to both its carboxylic acid form and its decarboxylated form.

The term tetrahydrocannabinol refers to both its carboxylic acid form and its decarboxylated from, which are also referred to as THC. The term cannabidiol refers to both its carboxylic acid form and its decarboxylated from, which are also referred to as CBD.

As used herein the term terpene refers to compounds comprising at least one isoprene unit. The terms terpene and terpenoid are used herein interchangeably.

As used herein the term "differs by at least 10%" means greater by at least 10% or smaller by at least 10%. For example, 10 and 12 differ by at least 10%. The same is true for 10 and 8.

Unless specified otherwise, all concentration and contents are in weight percent (% wt). Unless specified otherwise, all ratios are weight per weight ratios.

As used herein Ra/Rb refers to the ratio between Ra and Rb, i.e. to the product of dividing Ra by Rb.

The terms "provided solid *cannabis* plant material", "solid *cannabis* plant material", "*cannabis* plant material" and "plant material" are used interchangeably.

As used herein the term "extracting" refers to separating into another phase. Typically, extracting refers to separating components from a solid material, e.g. provided solid *cannabis* material, into a liquid phase or another solid phase. Alternatively, extracting refers to separating components from a solid material into a vapor phase, and optionally condensing said vapors.

As used herein the term "contacting a solid material with and extractant" means any form of contacting, e.g. washing the solid with the extractant, mixing the two or driving the extractant through a column containing the solid.

As used herein the term "*cannabis* plant material" means any part of a *cannabis* plant and any form of it.

As used herein the term "*cannabis* product compositions" means any composition derived from a *cannabis* plant.

As used herein the term "preferably decarboxylate one of the cannabinoids" means decarboxylation conducted at conditions wherein a cannabinoid is decarboxylated at a rate greater than that of another cannabinoid, e.g. by selecting a suitable decarboxylation temperature.

As used herein the term "first extractant is similar to second extractant" means that at least 90% of the composition are identical in both extractants.

DETAILED DESCRIPTION

An objective of the method of the first aspect is to form at least two different *cannabis* product compositions from a solid *cannabis* plant material, preferably the same *cannabis* plant material. The formed *cannabis* product compositions differ in the ratio between at least one cannabinoid and at least one terpene. According to an embodiment, the formed compositions differ in the ratio between a cannabinoid and multiple terpenes. According to an embodiment, the formed compositions differ in the ratio between multiple cannabinoid and a terpene. According to an embodiment, the formed compositions differ in the ratio between multiple cannabinoid and multiple terpenes. According to an embodiment, the formed compositions differ in the ratio between at least two cannabinoids.

First Aspect

According to a first aspect, provided is a method for the production of at least two different *cannabis* product compositions from a solid *cannabis* plant material comprising (i) providing a solid *cannabis* plant material comprising at least one cannabinoid and at least one non-cannabinoid at cannabinoid to non-cannabinoid weight/weight ratio R100; (ii) first extracting said solid *cannabis* plant material to form a first composition comprising at least 10% of the cannabinoid of said plant material and at least 1% of the non-cannabinoid of said plant material at cannabinoid to non-cannabinoid weight/weight ratio R101, wherein R101 differs from R100 by at least 10%; (iii) second extracting said solid *cannabis* plant material to form a second composition comprising at least 10% of the cannabinoid of said plant material and at least 1% of the non-cannabinoid of said plant material at cannabinoid to non-cannabinoid weight/weight ratio R102, wherein R102 differs from R101 by at least 10%; and (iv) optionally refining said first composition, said second composition or both. According to an embodiment, R102 differs from R100 by at least 10%. According to an embodiment, said non-cannabinoid is selected from the group consisting of terpenes, flavonoids and combinations thereof.

According to another facet of the first aspect, provided is a method for the production of at least two different *cannabis* product compositions from a solid *cannabis* plant material comprising (i) providing a solid *cannabis* plant material comprising at least one cannabinoid and at least one terpene at cannabinoid to terpene weight/weight ratio R100; (ii) first extracting said solid *cannabis* plant material to form a first composition comprising at least 10% of the cannabinoid of said plant material and at least 1% of the terpene in said plant material at cannabinoid to terpene weight/weight ratio R101, wherein R101 differs from R100 by at least 10%; (iii) second extracting said solid *cannabis* plant material to form a second composition comprising at least 10% of the cannabinoid of said plant material and at least 1% of the terpene in said plant material at cannabinoid to terpene weight/weight ratio R102, wherein R102 differs from R101 by at least 10%; and (iv) optionally refining said first composition, said second composition or both. According to an embodiment, R102 differs from R100 by at least 10%.

According to an embodiment, the cannabinoid of the first aspect is selected from the group consisting of tetrahydrocannabinol (THC) and cannabidiol (CBD).

According to an embodiment, said terpene is selected from the group consisting of pinenes, limonene, linalool, caryophyllene, myrcene, humulene, borneol, eucalyptol, terpineol and combinations thereof. According to an embodiment, said terpene has a boiling point in the range between 120° C. and 200° C. or between 140° C. and 180° C.

Any strain of *cannabis* plant is suitable. According to an embodiment said strain is selected from the strains listed in http://www.marijuana.com/strains/ and in https://www.leafly.com/explore. Any part of *cannabis* plant is suitable. According to an embodiment, the *cannabis* plant material comprises the flower of bud.

According to an embodiment, the cannabinoid to terpene weight/weight ratio in the provided solid *cannabis* plant material, R100, is in the range between 1:10 and 500:1, or between 1:1 and 200:1. According to an embodiment, the provided solid *cannabis* plant material comprises multiple cannabinoids (e.g. at least 2, at least 5, at least 10, at least 20, or at least 30) and/or multiple terpenes (e.g. at least 2, at least 4, at least 6, at least 8, or at least 10), so that there are multiple cannabinoid to terpene weight/weight ratios.

According to an embodiment, the method comprises drying said provided solid *cannabis* plant material, at least partially, prior to said first extracting. According to an embodiment said drying is conducted at about ambient temperature in an environment of controlled humidity. According to an embodiment, said plant material is dried to moisture content of less than 30% wt, less than 20% wt, less than 15% wt or less than 10% wt. According to an embodiment, said plant material is dried to moisture content of between 10% wt and 15% wt. According to an embodiment, the method further comprises heating the provided solid *cannabis* plant material prior to said first extracting or simultaneously with it. According to an embodiment, said heating is to a temperature in a range between 80° C. and 180° C., or between 100° C. and 160° C. According to an embodiment, said heating is for a duration between 1 minute and 2 hours, or between 10 minutes and 1.5 hours. According to an embodiment, said cannabinoid in said *cannabis* plant material is at least partially in its acid form and said heating temperature and duration are selected to effect decarboxylation of said cannabinoid. According to an embodiment, said heating temperature and duration are selected to effect partial decarboxylation of said cannabinoid, e.g. at least 10%, at least 20%, at least 30%, at least 40%, at least 50%, or at least 60%. According to an embodiment, said heating temperature and duration are selected to effect partial decarboxylation of said cannabinoid, e.g. at least 10%, but less than 90%, less than 80%, less than 70% or less than 60%.

Said first extracting said solid *cannabis* plant material forms a first composition. According to an embodiment said first composition is liquid, solid or a combination thereof. Said first composition comprises at least 10% of the cannabinoids in said plant material and at least 1% of the non-cannabinoid in said plant material. The extracted fractions of cannabinoids and of non-cannabinoids are controlled by parameters of extracting as is explained below.

According to an embodiment, said first composition comprises at least 10% wt of the cannabinoid in said provided solid plant material, at least 20% wt, at least 30% wt, at least 40% wt, at least 50% wt, at least 60% wt, at least 70% wt, or at least 80% wt. According to an embodiment, said solid *cannabis* plant material comprises multiple cannabinoids and said first composition comprises at least 10% wt of one of the cannabinoids in said provided solid plant material, at least 10% wt of multiple cannabinoids of said provided solid plant material, or at least 10% wt of total cannabinoids in said provided solid plant material. According to an embodiment, said first composition comprises less than 95% wt of the cannabinoid in said provided solid plant material, less than 90% wt, less than 80% wt, less than 70% wt, less than 60% wt, less than 50% wt, or less than 40% wt.

According to an embodiment, said first composition comprising at least 1% wt of the terpene in said provided solid plant material, at least 10% wt, at least 20% wt, at least 30% wt, at least 40% wt, at least 50% wt, at least 60% wt, at least 70% wt, or at least 80% wt. According to an embodiment, said solid *cannabis* plant material comprises multiple terpenes and said first composition comprises at least 1% wt of one of the terpenes in said provided solid plant material, at least 1% wt of multiple terpenes of said plant material, or at least 1% wt of total terpenes in said provided solid plant material.

In said formed first composition, cannabinoid to terpene weight/weight ratio, R101, differs from R100 by at least 10%. According to an embodiment, the provided solid *cannabis* plant material comprises multiple cannabinoids and/or multiple terpenes, so that there are multiple cannabinoid to terpene weight/weight ratios. According to an embodiment, the first composition comprises multiple cannabinoids and/or multiple terpenes, so that there are multiple cannabinoid to terpene weight/weight ratios. According to an embodiment, the ratio between a first cannabinoid and a first terpene in the first composition differs from the ratio between same cannabinoid and same terpene in the plant material by at least 10%. According to an embodiment, the same is true for the ratio between said first cannabinoid and a second terpene. According to an embodiment, the same is true for the ratio between a second cannabinoid and said first terpene. According to an embodiment, the same is true for the ratio between a second cannabinoid and a second terpene. According to an embodiment, the same is true for at least 2 ratios, at least 3, at least 4, at least 5, at least 6, at least 7, at least 8, at least 9 or at least 10 ratios.

According to an embodiment, R101 differs from R100 by at least 20%, at least 30%, at least 40%, at least 50%, at least 60%. According to an embodiment, R101/R100 is greater than 2, greater than 5, greater than 10 or greater than 20. According to an embodiment, R100/R101 is greater than 2, greater than 5, greater than 10 or greater than 20.

Said second extracting said solid *cannabis* plant material forms a second composition. According to an embodiment said second composition is liquid, solid or a combination thereof. Said second composition comprises at least 10% of said plant material cannabinoid and at least 1% of said plant material non-cannabinoid. The extracted fractions of cannabinoids and of non-cannabinoids are controlled by parameters of extracting as is explained below.

According to an embodiment, said second composition comprises at least 10% wt of the cannabinoid in said plant material cannabinoid, at least 20% wt, at least 30% wt, at least 40% wt, at least 50% wt, at least 60% wt, at least 70% wt, or at least 80% wt. According to an embodiment, said solid *cannabis* plant material comprises multiple cannabinoids and said second composition comprises at least 10% of one of the cannabinoids in said plant material, at least 10% of multiple of cannabinoids in said plant material, or at least 10% of total cannabinoids in said plant material.

According to an embodiment, said second composition comprises at least 1% wt of the terpene in said plant material, at least 10% wt, at least 20% wt, at least 30% wt, at least 40% wt, at least 50% wt, at least 60% wt, at least 70% wt, or at least 80% wt. According to an embodiment, said solid *cannabis* plant material comprises multiple terpenes and said second composition comprises at least 1% wt of one terpene of said plant material, at least 1% wt of multiple terpenes of said plant material, or at least 1% wt of total terpenes of said plant material.

In said formed second composition, cannabinoid to terpene weight/weight ratio, R102, differs from R101 by at least 10%. According to an embodiment, the provided solid *cannabis* plant material comprises multiple cannabinoids and/or multiple terpenes, so that there are multiple cannabinoid to terpene weight/weight ratios. According to an embodiment, the second composition comprises multiple cannabinoids and/or multiple terpenes, so that there are multiple cannabinoid to terpene weight/weight ratios.

According to an embodiment, the ratio between a first cannabinoid and a first terpene in the second composition differs from the ratio between same cannabinoid and same terpene in the first composition by at least 10%. According to an embodiment, the same is true for the ratio between said first cannabinoid and a second terpene. According to an embodiment, the same is true for the ratio between a second cannabinoid and said first terpene. According to an embodiment, the same is true for the ratio between a second cannabinoid and a second terpene. According to an embodiment, the same is true for at least 2 ratios, at least 3, at least 4, at least 5, at least 6, at least 7, at least 8, at least 9 or at least 10 ratios.

According to an embodiment, R102 differs from R101 by at least 20%, at least 30%, at least 40%, at least 50%, at least 60%. According to an embodiment, R102/R101 is greater than 2, greater than 5, greater than 10 or greater than 20. According to an embodiment, R101/R102 is greater than 2, greater than 5, greater than 10 or greater than 20.

According to an embodiment, R102 differs from R100 by at least 20%, at least 30%, at least 40%, at least 50%, at least 60%. According to an embodiment, R102/R100 is greater than 2, greater than 5, greater than 10 or greater than 20. According to an embodiment, R100/R102 is greater than 2, greater than 5, greater than 10 or greater than 20.

According to an embodiment, said plant material comprises a first cannabinoid and a second cannabinoid at first cannabinoid to second cannabinoid weight/weight ratio of R110; said first composition comprises said first cannabinoid and said second cannabinoid at first cannabinoid to second cannabinoid weight/weight ratio of R111, wherein R111 differs from R110 by at least 10%; and said second composition comprises said first cannabinoid and said second cannabinoid at first cannabinoid to second cannabinoid weight/weight ratio of R112, wherein R112 differs from R111 by at least 10%. According to an embodiment, R112 differs from R110 by at least 10%. According to an embodiment, said first cannabinoid is THC and said second cannabinoid is CBD.

According to an embodiment, R111 differs from R110 by at least 20%, at least 30%, at least 40%, at least 50%, at least 60%. According to an embodiment, R111/R110 is greater than 2, greater than 5, greater than 10 or greater than 20. According to an embodiment, R110/R111 is greater than 2, greater than 5, greater than 10 or greater than 20.

According to an embodiment, R112 differs from R111 by at least 20%, at least 30%, at least 40%, at least 50%, at least 60%. According to an embodiment, R112/R111 is greater than 2, greater than 5, greater than 10 or greater than 20. According to an embodiment, R111/R112 is greater than 2, greater than 5, greater than 10 or greater than 20.

According to an embodiment, R112 differs from R110 by at least 20%, at least 30%, at least 40%, at least 50%, at least 60%. According to an embodiment, R112/R110 is greater than 2, greater than 5, greater than 10 or greater than 20. According to an embodiment, R110/R112 is greater than 2, greater than 5, greater than 10 or greater than 20.

According to an embodiment, said first composition comprises both THC and CBD and THC/CBD weight/weight ratio in said first composition is greater than 2, greater than 5, greater than 10 or greater than 20.

According to an alternative embodiment, said first composition comprises both THC and CBD and CBD/THC weight/weight ratio in said first composition is greater than 2, greater than 5, greater than 10 or greater than 20.

According to an embodiment, said second composition comprises both THC and CBD and THC/CBD weight/ weight ratio in said second composition is greater than 2, greater than 5, greater than 10 or greater than 20.

According to an alternative embodiment, said second composition comprises both THC and CBD and CBD/THC weight/weight ratio in said second composition is greater than 2, greater than 5, greater than 10 or greater than 20.

According to an embodiment, said plant material comprises at least three cannabinoids and the weight ratio between the three in said first composition differs from the weight ratio between the three in the second composition by at least 10%.

The method of the first aspect is characterized in that the cannabinoid content of the provided solid *cannabis* material is divided into at least two compositions, optionally three, four, five or more. These compositions differ from each other in at least the weight/weight ratio between one cannabinoid and one terpene. According to an embodiment, the difference exists between at least 2 ratios, at least 3, at least 4, at least 5, at least 6, at least 7, at least 8, at least 9 or at least 10 ratios. Said dividing is effected by two or more extractions, each of which extracts a fraction of the cannabinoid and a fraction of at least one terpene. Extraction parameters are selected so that the fraction of the cannabinoid extracted differs from the fraction of at least one terpene.

According to an embodiment, said first extracting, said second extracting or both comprise contacting said provided solid *cannabis* material with an extractant, typically a liquid one. Said contacting of the solid *cannabis* plant material with liquid extractant results in a liquid solution comprising said extracted at least one cannabinoid and extracted at least one terpene, which liquid solution is also referred to as extract, and a solid residue comprising non-extracted cannabinoid and non-extracted terpene. According to an embodiment, the extract of the first extracting forms the first composition and the extract of the second extracting forms the second composition. According to an embodiment, at least one of said first extract and said second extract is further treated, e.g. for the removal of the extractant, for refining, for formulating or combinations thereof. According to an embodiment, said removal of the extractant comprises distilling the extractant. According to an embodiment, a terpene or multiple terpenes distill, at least partially along with said extractant. According to an embodiment, said refining comprises at least one of contact with an adsorbent, distillation and dewaxing. According to an embodiment, dewaxing comprises cooling and filtration. According to an embodiment, formulating comprises mixing with an oil, e.g. vegetable oil, with terpene or with plant extract, e.g. aroma plant extract.

According to an embodiment, the method further comprises combining the extract of the first extracting, the extract of the second extracting or both with a solid carrier. According to an embodiment, said combining comprises spraying the extract on said carrier prior to said removal of the extractant, simultaneously with it or after the removal of the extractant. Any carrier is suitable. According to an embodiment, said carrier is a plant material, e.g. a *cannabis* plant material. According to an alternative embodiment, said carrier comprises no cannabinoids before said spraying or comprises only CBD. According to an embodiment, said carrier is a porous solid material. According to an embodiment, said carrier is an internal part of a cartridge, e.g. a cartridge used in *cannabis* evaporators.

According to an embodiment, said first extracting comprises contacting with a first extractant. According to an embodiment, said second extracting comprises contacting with a second extractant. According to an embodiment, said first extractant, said second extractant, or both are selected from the group consisting of water, alkanols, super-critical $CO_2$, sub-critical $CO_2$, alkanes, alkenes, liquefied alkanes, liquefied alkenes, liquefied ethers and mixtures thereof. According to an embodiment, said alkanol is selected from the group consisting ethanol, propanols, butanols and mixtures thereof. According to an embodiment, said alkanes are C2-C6 alkanes. According to an embodiment, said alkenes are C2-C6 alkenes. According to an embodiment, said ether is dimethyl ether.

According to an embodiment, said first extractant, said second extractant, or both comprise an alkanol. According to an embodiment, said first extractant, said second extractant, or both comprise an aqueous alkanol solution. According to an embodiment, alkanol concentration in said extractant is at least 10% wt, at least 20% wt, at least 30% wt, at least 40% wt, at least 50% wt or at least 60% wt. According to an embodiment, alkanol concentration in said extractant is less than 95% wt, less than 90% wt, less than 80% wt, less than 70% wt, less than 60% wt or less than 50% wt. According to an embodiment, said alkanol forms an azeotrope with water and alkanol concentration in said extractant is within 20% of azeotrope concentration. According to an embodiment, alkanol concentration in said extractant is in the range between 30% wt and 70% wt or between 40% wt and 60% wt. According to an embodiment, said alkanol is ethanol.

According to an embodiment, said first extractant, said second extractant, or both further comprise *cannabis* plant material components. Typically the concentration of said *cannabis* plant material components in the extractant is less than 5%, less than 4%, less than 3%, less than 2%, or less than 1%. According to an embodiment, extractant separated from the extract is used at least partially in a following extracting step.

According to an embodiment said first extracting comprises contacting with a first extractant, said second extracting comprises contacting with a second extractant and said first extractant is similar to the second extractant or identical to it. As used herein, the term similar extractants refers to extractants wherein the concentrations of a major component (one that forms at least 50% of the extractant) are within 20% from each other. For example, an extractant comprising 60% ethanol is similar to an extractant comprising 70% ethanol.

According to an embodiment said first extracting comprises contacting with a first extractant comprising two solvents at a given weight/weight ratio, and said second extracting comprises contacting with a second extractant comprising those two solvents at a different ratio. According to an embodiment, both the first extractant and the second extractant comprise water and ethanol and the ethanol/water ratio in one of those is greater than the ratio in the second (as used herein, the term solvent refers also to water). For example, an extractant containing 66.6% wt ethanol and 33% wt water has ethanol/water ratio greater than that containing 50% wt ethanol and 50% wt water (ethanol/water ratios of 2 and 1, respectively). According to an embodiment, both the first extractant and the second extractant comprise $CO_2$ and ethanol and the $CO_2$/ethanol ratio in one of those is greater than the ratio in the second.

According to an embodiment, said first extractant comprises liquefied $CO_2$ at a first temperature and a first pressure, said second extractant comprises liquefied $CO_2$ at a second temperature and a second pressure and said first temperature differs from said second temperature and/or said first pressure differs from said second pressure.

According to an embodiment, said first extracting is conducted at a first temperature, said second extracting is conducted at a second temperature and said first temperature differs from said second temperature. According to an embodiment, said first extracting is conducted at a first pressure, said second extracting is conducted at a second pressure and said first pressure differs from said second pressure. According to an embodiment, said first extracting is conducted for a first duration, said second extracting is conducted at a second duration and said first duration differs from said second duration.

According to an embodiment, said first extracting, said second extracting or both comprise continuous, countercurrent contacting with an extractant.

According to an embodiment, said first extracting, said second extracting or both comprise distillation. According to an embodiment, said distillation is steam distillation. According to an embodiment, said steam distillation comprises contacting said provided plant material with steam, e.g. driving steam through it. According to an embodiment, between 1 Kg and 100 Kg steam is sued per 1 Kg of plant material. According to an embodiment, the method further comprises collecting the steam after said contacting and condensing it, whereby two phases are formed, one being essentially water and the other is said first composition and/or said second composition, respectively.

Said first extracting and said second extracting extract from the plant material cannabinoids and non-cannabinoid compounds, e.g. terpenes. Extraction parameters are typically designed to reach high yields, i.e. extraction of most, preferably the whole cannabinoids content of the plant material. Thus, e.g. in extraction comprising contacting with an extractant, the amount of extractant per 1 Kg plant material is typically large and contact duration is long enough to allow high yield. That is also the case with steam distillation, where steam amount and temperature are selected for high yield. Contrary to this typical practice, the parameters of first extracting in the present invention are selected to gain partial extraction of the cannabinoid in the plant material, e.g. more than 10%, but less than 90% wt, less than 80% wt, less than 70% wt, less than 60% wt, less than 50% wt, or less than 40% wt. The effects of various parameters on extraction yield chain between strains and depend on plant material preparation. Selecting the parameters for the method of the present invention may require pretesting of a sample of the provided plant material.

Typically, at least a fraction of the cannabinoid content of the solid *cannabis* plant material is in acid form. According to an embodiment, at least a fraction of the acid form cannabinoid is decarboxylated to the non-acid form, typically via heat treatment. According to an embodiment, said decarboxylating is conducted prior to said extracting. According to an alternative embodiment, said decarboxylating is conducted on the compositions formed.

According to still another embodiment, a partial decarboxylating is conducted prior to extracting or simultaneously with it and further decarboxylating is conducted on formed composition. According to a related embodiment, the solid *cannabis* plant material comprises at least two cannabinoids and the method of the first aspect comprises heating the plant material to preferably decarboxylate one of the cannabinoids prior to said first extracting or simultaneously with it. According to an alternative embodiment, the solid *cannabis* plant material comprises at least two cannabinoids and the method of the first aspect comprises heat treating the plant material to preferably decarboxylate one of the cannabinoids prior to said second extracting or simultaneously with it. While all the cannabinoids require elevated temperatures for decarboxylation, the decarboxylation rate dependence on temperature differ between the cannabinoids. According to an embodiment, preferable decarboxylating involves treatment at a temperature wherein one of the cannabinoids decarboxylates at a rate higher than that of another cannabinoid. For example, suppose at a temperature Ta, 50% of 1 gr of a first cannabinoid decarboxylates within 10 minutes, at a temperature Tb, 50% of 1 gr of second cannabinoid decarboxylates within 10 minutes and Tb is greater than Ta. According to an embodiment, in such case heating is conducted at a temperature under Tb, e.g. between Tb and Ta, at Ta or under Ta.

According to an embodiment, said method further comprises fractionating said first composition into a third composition with cannabinoid to terpene weight/weight ratio R103 and a fourth composition with cannabinoid to terpene weight/weight ratio R104, wherein R103 differs from R104 by at least 10%, at least 20%, at least 30%, at least 40%, at least 50% or at least 60%. According to an embodiment, R103/R104 is greater than 2, greater than 5, greater than 10 or greater than 20. According to an alternative embodiment, R104/R03 is greater than 2, greater than 5, greater than 10 or greater than 20. Fractionating is performed throughout by conventional methods such as contacting with an extractant and/or distillation, such as steam distillation.

According to an embodiment, said first composition comprises a first cannabinoid and a second cannabinoid; said third composition comprises said first cannabinoid and said second cannabinoid at first cannabinoid to second cannabinoid weight/weight ratio of R113; and said fourth composition comprises said first cannabinoid and said second cannabinoid at first cannabinoid to second cannabinoid weight/weight ratio of R114, wherein R114 differs from R113 by at least 10%, at least 20%, at least 30%, at least 40%, at least 50%, at least 60%. According to an embodiment, R114/R113 is greater than 2, greater than 5, greater than 10 or greater than 20. According to an alternative embodiment, R113/R114 is greater than 2, greater than 5, greater than 10 or greater than 20.

According to an embodiment, said method further comprises fractionating said second composition into a fifth composition with cannabinoid to terpene weight/weight ratio R105 and a sixth composition with cannabinoid to terpene weight/weight ratio R106, wherein R105 differs from R106 by at least 10% at least 20%, at least 30%, at least 40%, at least 50% or at least 60%. According to an embodiment, R105/R106 is greater than 2, greater than 5, greater than 10 or greater than 20. According to an embodiment, R106/R05 is greater than 2, greater than 5, greater than 10 or greater than 20.

According to an embodiment, said second composition comprises a first cannabinoid and a second cannabinoid; said fifth composition comprises said first cannabinoid and said second cannabinoid at first cannabinoid to second cannabinoid weight/weight ratio of R115; and said sixth composition comprises said first cannabinoid and said second cannabinoid at first cannabinoid to second cannabinoid weight/weight ratio of R116; wherein R116 differs from R115 by at least 10%, at least 20%, at least 30%, at least 40%, at least 50%, at least 60%. According to an embodiment, R116/R115 is greater than 2, greater than 5, greater than 10 or greater than 20. According to an embodiment, R115/R116 is greater than 2, greater than 5, greater than 10 or greater than 20.

According to an embodiment, said fractionating comprises at least one of contacting with an extractant and steam distillation.

According to an embodiment, said first extracting, said second extracting or both comprises contacting with a pressurized extractant, e.g. liquid CO2, liquefied alkanes and/or liquefied alkenes to form a pressurized extract comprising said extractant, at least one cannabinoid and at least one terpene. According to an embodiment, fractionating comprises partial pressure reduction, whereby two fractions are formed, one of which is high in the extractant and the other low in the extractant.

According to an embodiment, said fractionating comprises contacting with an ion-exchanger, e.g. an anion exchanger interacting with cannabinoid in acid form. According to an embodiment, said fractionating comprises chromatographic separation. According to an embodiment, said fractionating comprises distilling, e.g. at atmospheric pressure or at reduced pressure.

According to an embodiment, said method further comprises refining of at least one of said first composition, said second composition, said third composition, said fourth composition, said fifth composition, and said sixth composition. According to an embodiment, said refining comprises at least one of chromatographic separation, adsorption, filtration through active charcoal, dissolution in a suitable solvent followed by removal of non-soluble impurities and maintaining for several hours at low temperature, whereby impurities, such as waxes, precipitate out. According to an embodiment, said refining comprises removing at least one of alkaloids, flavonoids, carotenes, chlorophylls, terpenes, fats, waxes, carbohydrates, proteins and sugars.

According to an embodiment, said method further comprises providing at least one additional solid *cannabis* plant material of different cannabinoid and terpene content; first extracting said additional solid *cannabis* plant material to form a first additional composition comprising at least 10% of said additional plant material cannabinoid and at least 1% of said additional plant material; second extracting said additional solid *cannabis* plant material to form a second additional composition comprising at least 10% of said additional plant material cannabinoid and at least 1% of said additional plant material terpene and optionally refining said first additional composition, said second additional composition or both.

According to an embodiment, said method further comprises analysis of THC and CBD in at least one of said first composition, said second composition, said third composition, said fourth composition, said fifth composition, and said sixth composition.

According to an embodiment, said method further comprises formulating at least one of said compositions, optionally after refining, in an oil-comprising preparation. According to an embodiment, said method further comprises encapsulating at least one of said compositions, optionally after refining.

According to an embodiment, said method further comprises mixing composition formed according to any of the previous embodiments.

According to an embodiment, the first aspect further provides a composition formed according to any of the embodiments.

According to an embodiment, the first aspect further provides at least one product comprising a composition formed according to any of the embodiments. According to an embodiment, said product is selected from the group consisting of emulsions, solutions in various solvents, including oils and capsules containing said compositions. According to an embodiment, said product is selected from the group consisting of foods, food additives, animal feeds, beverages, cosmetic preparations, pharmaceuticals and nutraceuticals.

According to an embodiment, the first aspect further provides a method for treating a patient, comprising providing a composition according to any of the embodiments. According to an embodiment, the first aspect further provides a method for treating a patient, comprising providing multiple *cannabis* compositions according to any of the embodiments. According to an embodiment, the method further comprises providing to a patient several of said compositions, and selecting out of those the most suitable composition. According to an embodiment, said providing is via the skin, a mucosal tissue or both.

Second Aspect

According to a second aspect, provided is a method for the production of at least two different *cannabis* product compositions from a solid *cannabis* plant material comprising (i) providing a solid *cannabis* plant material comprising at least one cannabinoid and at least one non-cannabinoid; (ii) first extracting said plant material to form a first extract comprising at least 10% of said plant material cannabinoid and at least 1% of said plant material non-cannabinoid at cannabinoid to non-cannabinoid weight/weight ratio R200; (iii) fractionating said extract to form a first composition comprising at least 10% of said extract cannabinoid and at least 1%% of said extract non-cannabinoid at cannabinoid to non-cannabinoid weight/weight ratio R201 wherein R201 differs from R200 by at least 10%; and a second composition comprising at least 10% of said extract cannabinoid and at least 1% of said extract non-cannabinoid at cannabinoid to non-cannabinoid weight/weight ratio R202; wherein R202 differs from R201 by at least 10%; and (iv) optionally refining said first composition, said second composition or both. According to an embodiment, R202 differs from R200 by at least 10%.

According to an embodiment, said non-cannabinoid is selected from the group consisting of terpenes, flavonoids and combinations thereof.

According to another facet of the second aspect, provided is a method for the production of at least two different *cannabis* product compositions from a solid *cannabis* plant material comprising (i) providing a solid *cannabis* plant material comprising at least one cannabinoid and at least one terpene; (ii) first extracting said plant material to form a first extract comprising at least 10% of said plant material cannabinoid and at least 1% of said plant material terpene at cannabinoid to terpene weight/weight ratio R200; (iii) fractionating said extract to form a first composition comprising at least 10% of said extract cannabinoid and at least 1%% of said extract terpene at cannabinoid to terpene weight/weight ratio R201 wherein R201 differs from R200 by at least 10%; and a second composition comprising at least 10% of said extract cannabinoid and at least 1% of said extract terpene at cannabinoid to terpene weight/weight ratio R202; wherein R202 differs from R201 by at least 10%; and (iv) optionally refining said first composition, said second composition or both. According to an embodiment, R202 differs from R200 by at least 10%.

According to an embodiment, said method further comprises second extracting said solid *cannabis* plant material to form a third composition comprising at least 10% of said plant material cannabinoid and at least 1% of said plant material terpene. According to an embodiment, said method further comprises fractionating said third composition to form a fourth composition and a fifth composition, wherein the cannabinoid to terpene weight/weight ratio in said fourth composition differs from that ratio in the fifth composition by at least 10%.

According to an embodiment, the cannabinoid of the second aspect is selected from the group consisting of tetrahydrocannabinol and cannabidiol. According to an embodiment, said first cannabinoid is THC and said second cannabinoid is CBD.

According to an embodiment, said terpene is selected from the group consisting of pinenes, limonene, linalool, caryophyllene, myrcene, humulene, borneol, eucalyptol, terpineol and combinations thereof. According to an embodiment, said terpene has a boiling point in the range between 120° C. and 200° C. or between 140° C. and 180° C.

Any strain of *cannabis* plant is suitable. For example, any known strain selected from the strains listed in http://www.marijuana.com/strains/ and in https://www.leafly.com/explore are suitable. Any part of *cannabis* plant is suitable. According to an embodiment, the *cannabis* plant material comprises the flower of bud.

According to an embodiment, the cannabinoid to terpene weight/weight ratio in the provided solid *cannabis* plant material, R100, is in the range between 1:10 and 500:1, or between 1:1 and 200:1. According to an embodiment, the provided solid *cannabis* plant material comprises multiple cannabinoids (e.g. at least 2, at least 5, at least 10, at least 20, or at least 30) and/or multiple terpenes (e.g. at least 2, at least 4, at least 6, at least 8, or at least 10), so that there are multiple cannabinoid to terpene weight/weight ratios.

According to an embodiment, the method comprises drying said provided solid *cannabis* plant material, at least partially, prior to said first extracting. According to an embodiment aid drying is conducted at about ambient temperature in an environment of controlled humidity. According to an embodiment, said plant material is dried to moisture content of less than 30%, less than 20%, less than 15% or less than 10%. According to an embodiment, said plant material is dried to moisture content of between 10% wt and 15% wt. According to an embodiment, the method comprises heat treating the provided solid *cannabis* plant material prior to said first extracting or simultaneously with it. According to an embodiment, said heating is to a temperature in a range between 80° C. and 180° C., or between 100° C. and 160° C. According to an embodiment, said heating is for a duration between 1 minute and 2 hours, or between 10 minutes and 1.5 hours. According to an embodiment, said cannabinoid in said *cannabis* plant material is at least partially in its acid form and said heat treating temperature and duration are selected to achieve decarboxylation of said cannabinoid. According to an embodiment, said heating temperature and duration are selected to effect partial decarboxylation of said cannabinoid, e.g. at least 10%, at least 20%, at least 30%, at least 40%, at least 50%, or at least 60%. According to an embodiment, said heating temperature and duration are selected to effect partial decarboxylation of said cannabinoid, e.g. at least 10%, but less than 90%, less than 80%, less than 70% or less than 60%.

Said first extracting said solid *cannabis* plant material forms a first composition. According to an embodiment said first composition is liquid, solid or a combination thereof. Said first composition comprises at least 10% of the cannabinoids in said plant material and at least 1% of the non-cannabinoid in said plant material. The extracted fractions of cannabinoids and of non-cannabinoids are controlled by parameters of extracting as is explained in the first aspect.

According to an embodiment, said first extract comprises at least 10% of the cannabinoid in said plant material, at least 20%, at least 30%, at least 40%, at least 50%, at least 60%, at least 70%, or at least 80%. According to an embodiment, said *cannabis* plant material comprises multiple cannabinoids and said first extract comprises at least 10% of one of the cannabinoids in said plant material, at least 10% of multiple of cannabinoids in said plant material, or at least 10% of total cannabinoids in said plant material. According to an embodiment, said first extract comprises less than 95% of the cannabinoid in said provided solid plant material, less than 90%, less than 80%, less than 70%, less than 60%, less than 50%, or less than 40%.

According to an embodiment, said first extract comprises at least 1% of the terpene in said plant material, at least 10%, at least 20%, at least 30%, at least 40%, at least 50%, at least 60%, at least 70%, or at least 80%. According to an embodiment, said solid *cannabis* plant material comprises multiple terpenes and said first extract comprises at least 1% of one of the terpenes in said plant material, at least 1% of multiple terpenes of said plant material, or at least 1% of total terpenes in said plant material.

According to an embodiment, said first composition, said second composition or both comprise at least 10% of the cannabinoid of said first extract, at least 20%, at least 30%, at least 40%, at least 50%, at least 60%, at least 70%, or at least 80%. According to an embodiment, said first extract comprises multiple cannabinoids and said first composition, said second composition or both comprise at least 10% of one of the cannabinoids in said first extract, at least 10% of multiple cannabinoids of said first extract, or at least 10% of total cannabinoids of said first extract.

According to an embodiment, said first composition, said second composition of both comprise at least 1% of the terpene of said first extract, at least 10%, at least 20%, at least 30%, at least 40%, at least 50%, at least 60%, at least 70%, or at least 80%. According to an embodiment, said first extract comprises multiple terpenes and said first composition, said second composition or both comprise at least 1% of one of the terpenes of said first extract, at least 1% of multiple terpenes of said first extract, or at least 1% of the total terpenes of the first extract.

In said formed first composition of the second aspect, cannabinoid to terpene weight/weight ratio, R201, differs from R200 by at least 10%. According to an embodiment, the first extract comprises multiple cannabinoids and/or multiple terpenes, so that there are multiple cannabinoid to terpene weight/weight ratios. According to an embodiment, the first composition comprises multiple cannabinoids and/or multiple terpenes, so that there are multiple cannabinoid to terpene weight/weight ratios. According to an embodiment, the ratio between a first cannabinoid and a first terpene in the first composition differs from the ratio between same cannabinoid and same terpene in the first extract by at least 10%. According to an embodiment, the same is true for the ratio between said first cannabinoid and a second terpene. According to an embodiment, the same is true for the ratio between a second cannabinoid and said first terpene. According to an embodiment, the same is true for the ratio between a second cannabinoid and a second terpene. According to an embodiment, the same is true for at least 2 ratios, at least 3, at least 4, at least 5, at least 6, at least 7, at least 8, at least 9 or at least 10 ratios.

According to an embodiment, R201 differs from R200 by at least 20%, at least 30%, at least 40%, at least 50%, at least 60%. According to an embodiment, R201/R200 is greater than 2, greater than 5, greater than 10 or greater than 20.

According to an alternative embodiment, R200/R201 is greater than 2, greater than 5, greater than 10 or greater than 20.

According to an embodiment, in said formed second composition of the second aspect, cannabinoid to terpene weight/weight ratio, R202, differs from that of the first composition, R201, by at least 10%. According to an embodiment, the first composition comprises multiple cannabinoids and/or multiple terpenes, so that there are multiple cannabinoid to terpene weight/weight ratios. According to an embodiment, the second composition comprises multiple cannabinoids and/or multiple terpenes, so that there are multiple cannabinoid to terpene weight/weight ratios. According to an embodiment, the ratio between a first cannabinoid and a first terpene in the second composition differs from the ratio between same cannabinoid and same terpene in the first composition by at least 10%. According to an embodiment, the same is true for the ratio between said first cannabinoid and a second terpene. According to an embodiment, the same is true for the ratio between a second cannabinoid and said first terpene. According to an embodiment, the same is true for the ratio between a second cannabinoid and a second terpene. According to an embodiment, the same is true for at least 2 ratios, at least 3, at least 4, at least 5, at least 6, at least 7, at least 8, at least 9 or at least 10 ratios.

According to an embodiment, R202 differs from R201 by at least 20%, at least 30%, at least 40%, at least 50%, at least 60%. According to an embodiment, R202/R201 is greater than 2, greater than 5, greater than 10 or greater than 20. According to an alternative embodiment, R201/R202 is greater than 2, greater than 5, greater than 10 or greater than 20.

According to an embodiment, R202 differs from R200 by at least 20%, at least 30%, at least 40%, at least 50%, at least 60%. According to an embodiment, R202/R200 is greater than 2, greater than 5, greater than 10 or greater than 20. According to an alternative embodiment, R200/R202 is greater than 2, greater than 5, greater than 10 or greater than 20.

According to an embodiment, (a) said first extract comprises a first cannabinoid and a second cannabinoid (b) said first extract comprises said first cannabinoid and said second cannabinoid at first cannabinoid to second cannabinoid weight/weight ratio of R210; (c) said first composition comprises said first cannabinoid and said second cannabinoid at first cannabinoid to second cannabinoid weight/weight ratio of R211 wherein R211 differs from R210 by at least 10%; and (d) said second composition comprises said first cannabinoid and said second cannabinoid at first cannabinoid to second cannabinoid weight/weight ratio of R212, wherein R212 differs from R211 by at least 10%. According to an embodiment, said first cannabinoid is THC and said second cannabinoid is CBD.

According to an embodiment, R212 differs from R210 by at least 10%.

According to an embodiment, R211 differs from R210 by at least 20%, at least 30%, at least 40%, at least 50%, at least 60%. According to an embodiment, R211/R210 is greater than 2, greater than 5, greater than 10 or greater than 20. According to an alternative embodiment, R210/R211 is greater than 2, greater than 5, greater than 10 or greater than 20.

According to an embodiment, R212 differs from R211 by at least 20%, at least 30%, at least 40%, at least 50%, at least 60%. According to an embodiment, R212/R211 is greater than 2, greater than 5, greater than 10 or greater than 20.

According to an alternative embodiment, R211/R212 is greater than 2, greater than 5, greater than 10 or greater than 20.

According to an embodiment, R212 differs from R210 by at least 20%, at least 30%, at least 40%, at least 50%, at least 60%. According to an embodiment, R212/R210 is greater than 2, greater than 5, greater than 10 or greater than 20. According to an alternative embodiment, R210/R212 is greater than 2, greater than 5, greater than 10 or greater than 20.

According to an embodiment, said first composition comprises both THC and CBD and THC/CBD weight/weight ratio in said first composition is greater than 2, greater than 5, greater than 10 or greater than 20.

According to an alternative embodiment, said first composition comprises both THC and CBD and CBD/THC weight/weight ratio in said first composition is greater than 2, greater than 5, greater than 10 or greater than 20.

According to an embodiment, said second composition comprises both THC and CBD and THC/CBD weight/weight ratio in said second composition is greater than 2, greater than 5, greater than 10 or greater than 20.

According to an alternative embodiment, said second composition comprises both THC and CBD and CBD/THC weight/weight ratio in said second composition is greater than 2, greater than 5, greater than 10 or greater than 20.

The method of the second aspect is characterized in that the cannabinoid content of the provided solid *cannabis* material is divided into at least two compositions, optionally three, four or more. These compositions differ from each other by at least the weight/weight ratio between one cannabinoid and one terpene. According to an embodiment, the difference exists between at least 2 ratios, at least 3, at least 4, at least 5, at least 6, at least 7, at least 8, at least 9 or at least 10 ratios. Said dividing is effected by fractionating the first extract and optionally other extracts. Fractionation parameters are selected so that the fraction of the extract cannabinoid in a composition differs from the fraction of at least one extract terpene there.

According to an embodiment, said first extracting, said fractionating or both comprise at least one of contacting with an extractant and steam distillation.

According to an embodiment, said first extracting said fractionating or both comprise contacting with an extractant selected from the group consisting of water, alkanols, super-critical $CO_2$, sub-critical $CO_2$, alkanes, alkenes, liquefied alkanes, liquefied alkenes, liquefied ethers and mixtures thereof. According to an embodiment, said alkanol is selected from the group consisting ethanol, propanols, butanols and mixtures thereof. According to an embodiment, said alkanes are $C_2$-$C_6$ alkanes. According to an embodiment, said alkenes are $C_2$-$C_6$ alkenes. According to an embodiment, said ether is dimethyl ether.

According to an embodiment, said extractant comprises an alkanol. According to an embodiment, said first extractant, said second extractant, or both comprise an aqueous alkanol solution. According to an embodiment, alkanol concentration in said extractant is at least 10% wt, at least 20% wt, at least 30% wt, at least 40% wt, at least 50% wt or at least 60% wt. According to an embodiment, alkanol concentration in said extractant is less than 95% wt, less than 90% wt, less than 80% wt, less than 70% wt, less than 60% wt or less than 50% wt. According to an embodiment, said alkanol forms an azeotrope with water and alkanol concentration in said extractant is within 20% of azeotrope concentration. According to an embodiment, alkanol concentration in said extractant is in the range between 30% wt and 70% wt or between 40% wt and 60% wt. According to an embodiment, said alkanol is ethanol.

According to an embodiment said first extracting comprises contacting with a first extractant, said fractionating comprises contacting with a second extractant and said first extractant is similar to the second extractant or identical to it.

According to an embodiment said first extracting comprises contacting with a first extractant comprising two solvents at a given weight/weight ratio, and said fractionating comprises contacting with a second extractant comprising those two solvents at a different ratio. According to an embodiment, both the first extractant and the second extractant comprise water and ethanol and the water/ethanol ratio in one of those is greater than the ratio in the second. According to an embodiment, both the first extractant and the second extractant comprise $CO_2$ and ethanol and the $CO_2$/ethanol ratio in one of those is greater than the ratio in the second.

According to an embodiment, said first extractant comprises liquefied $CO_2$ at a first temperature and a first pressure, said second extractant comprises liquefied $CO_2$ at a second temperature and a second pressure and said first temperature differs from said second temperature and/or said first pressure differs from said second pressure.

According to an embodiment, extracting is conducted at a first temperature, fractionating is conducted at a second temperature and said first temperature differs from said second temperature. According to an embodiment, extracting is conducted at a first pressure, said fractionating is conducted at a second pressure and said first pressure differs from said second pressure. According to an embodiment, extracting is conducted for a first duration, fractionating is conducted at a second duration and said first duration differs from said second duration.

According to an embodiment, said first extracting, said second extracting or both comprise continuous, counter-current contacting with an extractant.

According to an embodiment, said first extracting comprises contacting with a pressurized extractant, e.g. liquid $CO_2$, liquefied alkanes and/or liquefied alkenes to form a pressurized extract comprising said extractant, at least one cannabinoid and at least one terpene. According to an embodiment, fractionating comprises partial pressure reduction, whereby two fractions are formed, one of which is high in the extractant and the other low in the extractant.

According to an embodiment, said first extracting, said fractionating or both comprise distillation. According to an embodiment, said distillation is steam distillation. According to an embodiment, said steam distillation comprises contacting said provided plant material with steam, e.g. driving steam through it. According to an embodiment, between 1 Kg and 100 Kg steam is sued per 1 Kg of plant material. According to an embodiment, the method further comprises collecting the steam after said contacting and condensing it, whereby two phases are formed, one being essentially water and the other is said first composition and/or said second composition, respectively.

Contrary to typical practice, the parameters of first extracting in the present invention are selected to gain partial extraction of the cannabinoid in the plant material, e.g. more than 10%, but less than 90% wt, less than 80% wt, less than 70% wt, less than 60% wt, less than 50% wt, or less than 40% wt.

According to an embodiment, said fractionating comprises contacting with an ion-exchanger, e.g. an anion exchanger interacting with cannabinoid in acid form. According to an embodiment, said fractionating comprises chromatographic separation. According to an embodiment, said fractionating comprises distilling, e.g. at atmospheric pressure or at reduced pressure.

Typically, at least a fraction of the cannabinoid content of the solid *cannabis* plant material is in acid form. According to an embodiment, at least a fraction of the acid form cannabinoid is decarboxylated to the non-acid form, typically via heat treatment. According to an embodiment, said decarboxylating is conducted prior to said first extracting and/or prior to said fractionating. According to an alternative embodiment, said decarboxylating is conducted on the compositions formed. According to still another embodiment, a partial decarboxylating is conducted prior to extracting, and/or prior to said fractionating and/or simultaneously with those and further decarboxylating is conducted on formed composition. According to a related embodiment, the solid *cannabis* plant material comprises at least two cannabinoids and the method of the first aspect comprises heat treating the plant material to preferably decarboxylate one of the cannabinoids prior to said first extracting or simultaneously with it. According to a related embodiment, the solid *cannabis* plant material comprises at least two cannabinoids and the method of the first aspect comprises heat treating the plant material to preferably decarboxylate one of the cannabinoids prior to said fractionating or simultaneously with it. According to an embodiment, preferable decarboxylating involves treatment at a temperature wherein one of the cannabinoids decarboxylates at a rate higher than that of another cannabinoid.

According to an embodiment, said method further comprises refining of at least one of said first composition, said second composition, said third composition, said fourth composition and said fifth composition. According to an embodiment, said refining comprises at least one of chromatographic separation, adsorption, filtration through active charcoal, dissolution in a suitable solvent followed by removal of non-soluble impurities and maintaining for several hours at low temperature, whereby impurities, such as waxes, precipitate out. According to an embodiment, said refining comprises removing at least one of alkaloids, flavonoids, carotenes, chlorophylls, terpenes, fats, waxes, carbohydrates, proteins and sugars.

According to an embodiment, said method of second aspect further comprises providing at least one additional solid *cannabis* plant material of different cannabinoid and terpene content; first extracting said additional solid *cannabis* plant material to form a first additional extract comprising at least 10% of said plant material cannabinoid and at least 1% of said plant material terpene; fractionating said first additional extract to form a first additional composition comprising at least 10% of said additional extract cannabinoid and at least 1%% of said additional extract terpene and a second additional composition comprising at least 10% of said extract cannabinoid and at least 1% of said extract terpene wherein the cannabinoid to terpene weight/weight ratio in said first additional composition differs from that ratio in the second additional composition by at least 10%.

According to an embodiment, said method further comprises analysis of THC and CBD in at least one of said first composition, said second composition, said third composition, said fourth composition, said fifth composition, and said additional compositions.

According to an embodiment, said method further comprises formulating at least one of said compositions, optionally after refining, in an oil-comprising preparation. According to an embodiment, said method further comprises encapsulating at least one of said compositions, optionally after refining.

According to an embodiment, said method further comprises mixing composition formed according to any of the previous embodiments.

According to an embodiment, the method further comprises combining said first composition, said second composition or both with a solid carrier. According to an embodiment, said combining comprises spraying the extract on said carrier prior to removal of the extractant, simultaneously with it or after the removal of the extractant. Any carrier is suitable. According to an embodiment, said carrier is a plant material, e.g. a *cannabis* plant material. According to an alternative embodiment, said carrier comprises no cannabinoids before said spraying or comprises only CBD. According to an embodiment, said carrier is a porous solid material. According to an embodiment, said carrier is an internal part of a cartridge, e.g. a cartridge used in *cannabis* evaporators.

According to an embodiment, the second aspect further provides a composition formed according to any of the embodiments. According to an embodiment, the second aspect further provides at least one product comprising a composition formed according to any of the embodiments. According to an embodiment, said products is selected from the group consisting of emulsions, solutions in various solvents, including oils and capsules containing said compositions. According to an embodiment, said product is selected from the group consisting of foods, food additives, animal feeds, beverages, cosmetic preparations, pharmaceuticals and nutraceuticals.

According to an embodiment, the second aspect further provides a method for treating a patient, comprising providing a composition according to any of the embodiments. According to an embodiment, the second aspect further provides a method for treating a patient, comprising providing multiple *cannabis* compositions according to any of the embodiments. According to an embodiment, the method further comprises providing to a patient several of said compositions, and selecting out of those the most suitable composition. According to an embodiment, said providing is via the skin, a mucosal tissue or both.

Third Aspect

According to a third aspect, provided is a method for the production of at least two different *cannabis* product compositions from a solid *cannabis* plant material comprising (i) providing a solid *cannabis* plant material comprising at least one cannabinoid and at least one non-cannabinoid at cannabinoid to non-cannabinoid weight/weight ratio R300; (ii) first extracting said solid *cannabis* plant material to form a first composition comprising at least 10%, but less than 90% of said provided solid plant material cannabinoid and at least 1% of said provided solid plant material non-cannabinoid at cannabinoid to non-cannabinoid weight/weight ratio R301, wherein R301 differs from R300 by at least 10%; and (iii) separating said first composition from the residual solid *cannabis* plant composition, which residual composition comprises at least 10% of said provided solid plant material cannabinoid and at least 1% of said provided solid plant material non-cannabinoid at cannabinoid to non-cannabinoid weight/weight ratio R302, wherein R302 differs from R301 by at least 10%. According to an embodiment R302 differs from R300 by at least 10%.

According to an embodiment, said non-cannabinoid is selected from the group consisting of terpenes, flavonoids and combinations thereof.

According to another facet of the third aspect, provided is a method for the production of at least two different *cannabis* product compositions from a solid *cannabis* plant material comprising (i) providing a solid *cannabis* plant material comprising at least one cannabinoid and at least one terpene at cannabinoid to terpene weight/weight ratio R300; (ii) first extracting said solid *cannabis* plant material to form a first composition comprising at least 10%, but less than 90% of said provided solid plant material cannabinoid and at least 1% of said provided solid plant material terpene at cannabinoid to terpene weight/weight ratio R301, wherein R301 differs from R300 by at least 10%; and (iii) separating said first composition from the residual solid *cannabis* plant composition, which residual composition comprises at least 10% of said provided solid plant material cannabinoid and at least 1% of said provided solid plant material terpene at cannabinoid to terpene weight/weight ratio R302, wherein R302 differs from R301 by at least 10%. According to an embodiment R302 differs from R300 by at least 10%.

According to an embodiment, said first composition comprises at least 10% of said provided solid plant material cannabinoid, at least 20%, at least 30%, at least 40%, at least 50%, at least 60%, at least 70%, or at least 80%. According to an embodiment, said solid *cannabis* plant material comprises multiple cannabinoids and said first composition comprises at least 10% of one of said provided solid plant material cannabinoids, at least 10% of multiple of said provided solid plant material cannabinoids, or at least 10% of total provided solid plant material cannabinoids. According to an embodiment, said first composition comprises less than 90% of said provided solid plant material cannabinoid, less than 90%, less than 80%, less than 70%, less than 60%, less than 50%, or less than 40%.

According to an embodiment, said first composition comprising at least 1% of said provided solid plant material terpene, at least 10%, at least 20%, at least 30%, at least 40%, at least 50%, at least 60%, at least 70%, or at least 80%. According to an embodiment, said solid *cannabis* plant material comprises multiple terpenes and said first composition comprises at least 1% of one of said provided solid plant material terpenes, at least 1% of multiple of said plant material terpenes, or at least 1% of total provided solid plant material terpenes.

In said formed first composition, cannabinoid to terpene weight/weight ratio, R301, differs from R300 by at least 10%. According to an embodiment, the provided solid *cannabis* plant material comprises multiple cannabinoids (e.g. at least 2, at least 5, at least 10, at least 20, or at least 30) and/or multiple terpenes (e.g. at least 2, at least 4, at least 6, at least 8, or at least 10), so that there are multiple cannabinoid to terpene weight/weight ratios. According to an embodiment, the first composition comprises multiple cannabinoids and/or multiple terpenes, so that there are multiple cannabinoid to terpene weight/weight ratios. According to an embodiment, the ratio between a first cannabinoid and a first terpene in the first composition differs from the ratio between same cannabinoid and same terpene in the plant material by at least 10%. According to an embodiment, the same is true for the ratio between said first cannabinoid and a second terpene. According to an embodiment, the same is true for the ratio between a second cannabinoid and said first terpene. According to an embodiment, the same is true for the ratio between a second cannabinoid and a second terpene. According to an embodiment, the same is true for at least 2 ratios, at least 3, at least 4, at least 5, at least 6, at least 7, at least 8, at least 9 or at least 10 ratios.

According to an embodiment, R301 differs from R300 by at least 20%, at least 30%, at least 40%, at least 50%, at least 60%. According to an embodiment, R301/R300 is greater than 2, greater than 5, greater than 10 or greater than 20. According to an alternative embodiment, R300/R301 is greater than 2, greater than 5, greater than 10 or greater than 20.

According to an embodiment, said residual solid *cannabis* plant composition comprises at least 10% of said provided solid plant material cannabinoid, at least 20%, at least 30%, at least 40%, at least 50%, at least 60%, at least 70%, or at least 80%. According to an embodiment, said solid *cannabis* plant material comprises multiple cannabinoids and said residual solid *cannabis* plant composition comprises at least 10% of one of said provided solid plant material cannabinoids, at least 10% of multiple of said provided solid plant material cannabinoids, or at least 10% of total provided solid plant material cannabinoids. According to an embodiment, said residual solid *cannabis* plant composition comprises less than 95% of said provided solid plant material cannabinoid, less than 90%, less than 80%, less than 70%, less than 60%, less than 50%, or less than 40%.

According to an embodiment, said residual solid *cannabis* plant composition comprises at least 1% of said provided solid plant material terpene, at least 10%, at least 20%, at least 30%, at least 40%, at least 50%, at least 60%, at least 70%, or at least 80%. According to an embodiment, said solid *cannabis* plant material comprises multiple terpenes and said residual solid *cannabis* plant composition comprises at least 1% of one of said provided solid plant material terpenes, at least 1% of multiple of said plant material terpenes, or at least 1% of total provided solid plant material terpenes.

In said formed residual solid *cannabis* plant composition, cannabinoid to terpene weight/weight ratio, R301, differs from R300 by at least 10%. According to an embodiment, the provided solid *cannabis* plant material comprises multiple cannabinoids and/or multiple terpenes, so that there are multiple cannabinoid to terpene weight/weight ratios. According to an embodiment, the residual solid *cannabis* plant composition comprises multiple cannabinoids and/or multiple terpenes, so that there are multiple cannabinoid to terpene weight/weight ratios. According to an embodiment, the ratio between a first cannabinoid and a first terpene in the residual solid *cannabis* plant composition differs from the ratio between same cannabinoid and same terpene in the plant material by at least 10%. According to an embodiment, the same is true for the ratio between said first cannabinoid and a second terpene. According to an embodiment, the same is true for the ratio between a second cannabinoid and said first terpene. According to an embodiment, the same is true for the ratio between a second cannabinoid and a second terpene. According to an embodiment, the same is true for at least 2 ratios, at least 3, at least 4, at least 5, at least 6, at least 7, at least 8, at least 9 or at least 10 ratios.

According to an embodiment, R302 differs from R302 by at least 20%, at least 30%, at least 40%, at least 50%, at least 60%. According to an embodiment, R302/R301 is greater than 2, greater than 5, greater than 10 or greater than 20. According to an alternative embodiment, R301/R302 is greater than 2, greater than 5, greater than 10 or greater than 20.

According to an embodiment, said provided solid *cannabis* plant material comprises a first cannabinoid and a second cannabinoid at first cannabinoid to second cannabinoid weight/weight ratio of R310; said first composition comprises said first cannabinoid and said second cannabinoid at first cannabinoid to second cannabinoid weight/weight ratio of R311, wherein R311 differs from R310 by at least 10%; and said residual solid composition comprises said first cannabinoid and said second cannabinoid at first cannabinoid to second cannabinoid weight/weight ratio of R312, wherein R312 differs from R311 by at least 10%. According to an embodiment R312 differs from R310 by at least 10%.

According to an embodiment, R311 differs from R310 by at least 20%, at least 30%, at least 40%, at least 50%, at least 60%. According to an embodiment, R311/R310 is greater than 2, greater than 5, greater than 10 or greater than 20. According to an embodiment, R310/R311 is greater than 2, greater than 5, greater than 10 or greater than 20.

According to an embodiment, R312 differs from R311 by at least 20%, at least 30%, at least 40%, at least 50%, at least 60%. According to an embodiment, R312/R311 is greater than 2, greater than 5, greater than 10 or greater than 20. According to an embodiment, R311/R312 is greater than 2, greater than 5, greater than 10 or greater than 20.

According to an embodiment, R312 differs from R310 by at least 20%, at least 30%, at least 40%, at least 50%, at least 60%. According to an embodiment, R312/R310 is greater than 2, greater than 5, greater than 10 or greater than 20. According to an embodiment, R310/R312 is greater than 2, greater than 5, greater than 10 or greater than 20.

According to an embodiment, said first composition comprises both THC and CBD and THC/CBD weight/weight ratio in said first composition is greater than 2, greater than 5, greater than 10 or greater than 20.

According to an alternative embodiment, said first composition comprises both THC and CBD and CBD/THC weight/weight ratio in said first composition is greater than 2, greater than 5, greater than 10 or greater than 20.

According to an embodiment, said residual solid *cannabis* plant composition comprises both THC and CBD and THC/CBD weight/weight ratio in said second composition is greater than 2, greater than 5, greater than 10 or greater than 20.

According to an alternative embodiment, said residual solid *cannabis* plant composition comprises both THC and CBD and CBD/THC weight/weight ratio in said second composition is greater than 2, greater than 5, greater than 10 or greater than 20.

According to an embodiment, said plant material comprises at least three cannabinoids and the weight ratio between the three in said first composition differs from the weight ratio between the three in the second composition by at least 10%.

According to an embodiment, the cannabinoid of the third aspect is selected from the group consisting of tetrahydrocannabinol and cannabidiol. According to an embodiment, said first cannabinoid is tetrahydrocannabinol and said second cannabinoid is cannabidiol.

According to an embodiment, said terpene is selected from the group consisting of pinenes, limonene, linalool, caryophyllene, myrcene, humulene, borneol, eucalyptol, terpineol and combinations thereof. According to an embodiment, said terpene has a boiling point in the range between 120° C. and 200° C. or between 140° C. and 180° C.

Any strain of *cannabis* plant is suitable. According to an embodiment said strain is selected from the strains listed in http://www.marijuana.com/strains/ and in https://www.leafly.com/explore. Any part of *cannabis* plant is suitable. According to an embodiment, the *cannabis* plant material comprises the flower of bud.

According to an embodiment, R300, is in the range between 1:10 and 500:1, or between 1:1 and 1:200.

According to an embodiment, the method further comprises drying said provided solid *cannabis* plant material. According to various embodiments, drying is conducted according to drying embodiments described above, for, example, in the first aspect. According to an embodiment, the method further comprises heating the provided solid

*cannabis* plant material. According to various embodiments, heating is conducted according to heating embodiments described above, for example, in the first aspect.

According to an embodiment, said solid *cannabis* plant material comprises at least two cannabinoids and the method further comprises heating the plant material to preferably decarboxylate one of the cannabinoids prior to said first extracting or simultaneously with it. According to various embodiments, heating for decarboxylation is conducted as described above, for example, according to heating embodiments described in the first aspect According to an embodiment said first extracting comprises at least one of contacting with a first extractant and steam distillation.

According to an embodiment said first extracting comprises contacting with a first extractant selected from the group consisting of water, alkanols, super-critical $CO_2$, sub-critical $CO_2$, alkanes, alkenes, liquefied alkanes, liquefied alkenes, liquefied ethers, and mixtures thereof. According to various embodiment said first extractant is selected as described above, for example, according to embodiments of the extractant described in the first aspect.

According to an embodiment said first extracting comprises steam distillation. According to various embodiments, steam distillation is conducted according to steam distillation embodiments described above, for example, as described in the first aspect According to an embodiment, said method further comprises heat treating of said first composition.

According to an embodiment, said method further comprises fractionating said first composition into a third composition with cannabinoid to terpene weight/weight ratio R303 and a fourth composition with cannabinoid to terpene weight/weight ratio R304, wherein R303 differs from R304 by at least 10%. According to an embodiment, said first composition comprises a first cannabinoid and a second cannabinoid, first cannabinoid to second cannabinoid weight/weight ratio in said third composition is R313, first cannabinoid to second cannabinoid weight/weight ratio in said fourth composition is R314, and R313 differs from R314 by at least 10%.

According to an embodiment, the method further comprises combining the extract of the first extracting, with a solid carrier. According to an embodiment, said combining comprises spraying the extract on said carrier prior to removal of the extractant, simultaneously with it or after the removal of the extractant. Any carrier is suitable. According to an embodiment, said carrier is a plant material, e.g. a *cannabis* plant material. According to an alternative embodiment, said carrier comprises no cannabinoids before said spraying or comprises only CBD. According to an embodiment, said carrier is a porous solid material. According to an embodiment, said carrier is an internal part of a cartridge, e.g. a cartridge used in *cannabis* evaporators.

According to an embodiment, the third aspect further provides a composition formed according to any of the embodiments.

According to an embodiment, the third aspect further provides a residual solid *cannabis* plant composition formed according to any of the embodiments.

According to an embodiment, the third aspect further provides at least one product comprising a composition formed according to any of the embodiments. According to an embodiment, said products is selected from the group consisting of emulsions, solutions in various solvents, including oils and capsules containing said compositions.

According to an embodiment, the third aspect further provides products comprising a residual solid *cannabis* plant composition formed according to any of the embodiments. According to an embodiment, said products are selected from emulsions, capsules and cigarettes. According to an embodiment, said product is selected from the group consisting of foods, food additives, animal feeds, beverages, cosmetic preparations, pharmaceuticals and nutraceuticals.

According to an embodiment, the third aspect further provides a method for treating a patient, comprising providing a composition according to any of the embodiments. According to an embodiment, the third aspect further provides a method for treating a patient, comprising providing a residual solid *cannabis* plant composition according to any of the embodiments. According to an embodiment, the third aspect further provides a method for treating a patient, comprising providing multiple *cannabis* compositions according to any of the embodiments. According to an embodiment, the method further comprises providing to a patient several of said compositions, and selecting out of those the most suitable composition. According to an embodiment, said providing is via the skin, a mucosal tissue or both.

EXAMPLES

Example 1: Plant Material Preparation and Analysis

Buds of Magen strain grown by IMC Israel was dried at ambient temperature and at controlled moisture. It was then ground and mixed well for homogenization. Moisture content was found to be 11.2% wt. A sample of the ground material was analyzed. The results are shown in Table 1:

TABLE 1

| CBDV | CBDA | CBG | CBD | CBGA | CBN | THC | CBC | THCA | Total THC | Total CBD | Total CBG | Total CBD/ THC | THCA THC | CBDA/ CBD | Total terpene mg/gr |
|------|------|-----|-----|------|-----|-----|-----|------|-----------|-----------|-----------|----------------|----------|-----------|---------------------|
| 0.02 | 9.02 | 0.04 | 0.76 | 0.40 | 0.06 | 1.21 | 0.06 | 6.37 | 6.80 | 8.67 | 0.39 | 1.27 | 5.26 | 11.9 | 108 |

CBDV—Cannabidivarin;
CBDA—Cannabidiolic Acid;
CBG—Cannabigerol;
CBD—Cannabidiol;
CBGA—Cannabigerolic acid;
CBN—Cannabinol;
THC—tetrahydrocannabinol;
CBC—Cannabichromene;
THCA—tetrahydrocannabinolic acid
Total THC: THC + THC content of THCA;
Total CBD: CBD + CBD content of THCA;

Example 2: Extraction with 95% Ethanol

Ground plant material prepared according to Example 1 was extracted by mixing with 95% ethanol at ambient temperature for 10 minutes. Two experiments were conducted. In one of them (2.1) the extractant to plant material ratio was 10:1 weight/weight. In the other (2.2) it was 4.2:1 weight/weight. The extracts formed were separated from the residual plant material and analyzed.

Table 2 summarizes the analyses calculated back to plant material amount. Also shown are the amounts of total THC and total CBD extracted as a fraction of the initial amounts of total THC and total CBD, respectively, in the plant material.

TABLE 2

| | CBDA | CBD | CBGA | CBN | THC | CBC | THCA | Total THC | Total CBD | Total CBG | Total CBD/ THC | THCA THC | CBDA/ CBD | Total terpenes mg/gr |
|---|---|---|---|---|---|---|---|---|---|---|---|---|---|---|
| 2.1 | 7.8 | 0.71 | 0.33 | 0.05 | 1.04 | 0.05 | 5.45 | 5.82 | 7.6 | 0.32 | 1.11 | 5.25 | 11.0 | 14 |
| % Ext | | | | | | | | 87 | 87 | | | | | 13 |
| 2.2 | 15.5 | 1.75 | 0.79 | 0.12 | 2.52 | 0.12 | 12.2 | 13.2 | 15.3 | 0.75 | 1.15 | 4.84 | 8.9 | |
| % Ext | | | | | | | | 82 | 74 | | | | | |

In both 2.1 and 2.2 a large fraction of both total THC and total CBD were extracted. The total CBD/total THC ratios in the two extracts, 1.11 and 1.15 are quite similar to that in the extracted plant material. Yet, while 87% of total THC and total CBD were extracted in 2.1, only 13% of the total terpenes amount was extracted, so that terpene/THC and terpene/CBD ratios in the extract are about 40 times smaller than those in the residual plat material.

Example 3: Effect of Ethanol Concentration

Ground plant material prepared according to Example 1 was extracted by mixing with ethanol solutions of various concentration at ambient temperature for 10 minutes. In all of them, the extractant to plant material ratio was 10:1 weight/weight. The extracts formed were separated from the residual plant material and analyzed.

Table 3 summarizes the analyses of total THC and total CBD calculated back to plant material amount. Also shown are the amounts of total THC and total CBD extracted as a fraction of the initial amounts of total THC and total CBD, respectively, in the plant material.

TABLE 3

| Ethanol Conc. (% wt) | Total CBD | Total THC | Total CBD/total THC |
|---|---|---|---|
| 90 | 8.5 | 6.9 | 1.23 |
| % Ext | 99 | 96 | |
| 78 | 7.2 | 5.7 | 1.26 |
| % Ext | 84 | 79 | |
| 70 | 7.6 | 6.0 | |
| % Ext | 88 | 83 | 1.27 |
| 60 | 7.4 | 5.2 | 1.42 |
| % Ext | 86 | 72 | |
| 55 | 6.3 | 3.7 | 1.70 |
| % Ext | 73 | 51 | |
| 50 | 4.1 | 1.8 | 2.3 |
| % Ext | 48 | 25 | |

These results show that the selectivity to CBD increases with decreasing extent of extraction and decreasing concentration of the ethanol. On extraction with 50% wt ethanol, total CBD/total THC ratio in the extract is about 3 times greater than that in the residual plant material.

Example 4: Two Steps Extraction with 50% Wt Ethanol

Ground plant material prepared according to Example 1 was extracted first by mixing with 50% wt ethanol at extractant to plant material ratio of 10:1 weight/weight and at ambient temperature for 10 minutes. About 70% of the first extract were separated and replaced with the same amount of fresh 50% wt ethanol. Second extraction was conducted similarly to the first one. The two extracts and the residual plant material were analyzed.

Table 4 summarizes the analyses calculated back to plant material amount. Also shown are the amounts of total THC and total CBD extracted as a fraction of the initial amounts of total THC and total CBD, respectively, in the plant material.

TABLE 4

| | CBDA | CBD | CBGA | CBN | THC | CBC | THCA | Total THC | Total CBD | Total CBG | Total CBD/ THC | THCA THC | CBDA/ CBD | Total terpenes mg/gr |
|---|---|---|---|---|---|---|---|---|---|---|---|---|---|---|
| 1$^{st}$ | 4.3 | 0.26 | 0.16 | 0.01 | 0.14 | 0.01 | 1.08 | 1.08 | 3.98 | 0.14 | 3.68 | 7.7 | 16.5 | 13 |
| % Ex | | | | | | | | 16 | 46% | | | | | 12 |
| 2$^{nd}$ | 2.65 | 0.2 | 0.1 | 0.01 | 0.15 | 0.01 | 1.05 | 1.05 | 2.55 | | 2.42 | 7.0 | 13.2 | 20 |
| | | | | | | | | 15 | 29 | | | | | 18 |
| Res. | | | | | | | | 4.69 | 4.34 | | 0.93 | | 7.4 | |

Total CBD/total THC weight/weight in the first extract, in the second extract and in the residual plant material are, 3.68, 2.42 and 0.93 respectively. Compared with the ratio in the initial plant material, these are 290%, 190% and 73%, respectively.

Comparing the extraction of cannabinoids to that of terpenes, the terpenes/total CBD ratios in the second extract is 2.2 times greater than that in the first.

Additionally, CBDA/CBD ratios in the initial plant material, first extract, second extract and residual plant material are 11.9, 16.5, 13.2 and 7.4, respectively.

Example 5: Four Steps Extraction with 50% Wt Ethanol

The experiment in Example 4 was repeated, this time conducting four extraction steps. Note that the fraction of extract removed after the 10 minutes mixing changes from one step to the other because of experimental difficulties.

Table 5 summarizes the analyses calculated back to plant material amount.

TABLE 5

| Extraction step | Total CBD | Total THC | Total CBD/Total THC |
|---|---|---|---|
| $1^{st}$ | 4.3 | 1.7 | 2.5 |
| $2^{nd}$ | 2.7 | 1.6 | 1.7 |
| $3^{rd}$ | 1.7 | 1.3 | 1.3 |
| $4^{th}$ | 1.0 | 1.0 | 1.0 |

Four extracts are formed with different total CBD/total THC weight/weight ratios. Compared with that ratio in the initial plant material, those are 200%, 134%, 100% and 79%.

Example 6: The Effect of Pre-Heating

Ground plant material prepared according to Example 1 was kept at 100° C. for 15 minutes. Then it was cooled, an example of it was kept for analyses and the rest was extracted once with 50% ethanol, using same temperature, extract/plat material ratio and mixing time as in Example 4. The extract and the residual plant material were also analyzed. The results are summarized in Table 6, calculated back to plant material amount.

TABLE 6

| | CBDA | CBD | CBGA | CBN | THC | CBC | THCA | Total THC | Total CBD | Total CBG | Total CBD/ THC | THCA THC | CBDA/ CBD | Total terpenes mg/gr |
|---|---|---|---|---|---|---|---|---|---|---|---|---|---|---|
| Heated | 9.43 | 1.37 | 0.40 | 0.07 | 2.18 | 0.11 | 6.09 | 7.52 | 9.64 | 0.40 | 1.28 | 2.79 | 6.9 | 106 |
| Extract | 4.55 | 0.36 | 0.16 | 0.02 | 0.22 | 0.01 | 1.22 | 1.30 | 4.31 | 0.16 | 3.3 | 5.55 | 12.6 | 13 |
| % Ex | | | | | | | | 17 | 45 | | | | | |
| Res | 3.58 | 3.15 | 0.15 | 0.09 | 3.96 | 0.22 | 1.59 | 5.35 | 6.28 | 0.32 | 1.17 | 0.40 | 1.14 | 19 |

THCA/THC weight/weight ratios for the plant material, the heat treated plant material, the extract and the residual plant material are 5.3, 2.8, 5.6 and 0.4, respectively indicating preferred extraction of the acid form over the decarboxylated form. The same is true for CBDA/CBD weight/weight ratios: 11.9, 6.9, 12.6 and 1.14, respectively.

The invention claimed is:

1. A method for the production of two different *cannabis* flower extracts from an initial solid *cannabis* flower material, the method consisting essentially of:
    providing an initial solid *cannabis* flower material whose cannabinoids consist essentially of a compound selected from the group consisting of tetrahydrocannabinol and cannabidiol and whose terpenes consist essentially of at least one terpene selected from the group consisting of pinene, limonene, linalool, caryophyllene, myrcene, humulene, borneol, eucalyptol, terpineol and mixtures thereof;
    extracting said initial solid *cannabis* flower material wherein a first *cannabis* flower extract and a first residual solid *cannabis* flower composition are formed,
    wherein said extracting consists essentially of extracting said initial solid *cannabis* flower material with ethanol, and
    wherein said first *cannabis* flower extract cannabinoids consist essentially of tetrahydrocannabinol and cannabidiol in an amount that is at least 10% but less than 80% of the amount of said tetrahydrocannabinol and cannabidiol in said initial solid *cannabis* flower material, and wherein said first *cannabis* flower extract terpenes consist essentially of said at least one terpene selected from the group consisting of pinene, limonene, linalool, caryophyllene, myrcene, humulene, borneol, eucalyptol, terpineol and mixtures thereof in an amount that is at least 10% of the amount of said at least one terpene in said initial solid *cannabis* flower material;
    separating said first residual solid *cannabis* flower composition from said first *cannabis* flower extract to yield a separated first *cannabis* flower extract; and
    extracting said first residual solid *cannabis* flower composition with ethanol to yield a second *cannabis* flower extract composition,
    wherein said extracting consists essentially of extracting said first residual solid *cannabis* flower composition with ethanol to yield the second *cannabis* flower extract composition, and
    wherein said second *cannabis* flower extract cannabinoids consist essentially of said tetrahydrocannabinol and cannabidiol in an amount that is at least 10% of the amount of said tetrahydrocannabinol and cannabidiol in said initial solid *cannabis* flower material, and wherein said second *cannabis* flower extract terpenes consist essentially of said at least one terpene selected from the group consisting of pinene, limonene, linalool, caryophyllene, myrcene, humulene, borneol, eucalyptol, terpineol and mixtures thereof in an amount that is at least 1% of the amount of said at least one terpene selected from the group consisting of pinene, limonene, linalool, caryophyllene, myrcene, humulene, borneol, eucalyptol, terpineol and mixtures thereof in said initial solid *cannabis* flower material,
    wherein a concentration of about 40% ethanol to about 60% ethanol is used for any of
        a) said extracting of said initial solid *cannabis* flower material, and
        b) said extracting of said first residual solid *cannabis* flower extract composition,
    wherein extracting said initial solid *cannabis* flower material with ethanol at a concentration of from about 40% to about 60% provides a total cannabidiol to tetrahydrocannabinol ratio in said first *cannabis* flower extract composition which is greater than a total cannabidiol to tetrahydrocannabinol ratio in said initial solid *cannabis* flower material, and wherein extracting said first residual solid *cannabis* flower composition with ethanol at a concentration of from about 40% to about 60% provides a total cannabidiol to tetrahydrocannabinol ratio in said second *cannabis* flower extract composition which is greater than a total cannabidiol to tetrahydrocannabinol ratio in said first residual solid *cannabis* flower composition.

* * * * *